United States Patent
McEwen (12)

(10) Patent No.: US 6,361,548 B1
(45) Date of Patent: Mar. 26, 2002

(54) LIMB PROTECTION SLEEVE FOR MATCHING TOURNIQUET CUFF

(76) Inventor: James Allen McEwen, 10551 Bamberton Drive, Richmond, B.C. (CA), V7A 1K6

( * ) Notice: Subject to any disclaimer, the term of this patent is extended or adjusted under 35 U.S.C. 154(b) by 0 days.

(21) Appl. No.: 09/378,034

(22) Filed: Aug. 20, 1999

(51) Int. Cl.[7] ............................................. A61B 17/00
(52) U.S. Cl. .................................... 606/201; 602/202
(58) Field of Search ............................. 606/201, 202, 606/203, 204

(56) References Cited

U.S. PATENT DOCUMENTS

| | | |
|---|---|---|
| 4,406,281 A | 9/1983 | Hubbard |
| 4,469,099 A | 9/1984 | McEwen |
| 4,635,635 A | 1/1987 | Robinette-Lehman |
| 4,637,394 A | 1/1987 | Racz |
| 4,650,475 A * | 3/1987 | Smith et al. ................ 604/189 |
| 4,869,265 A | 9/1989 | McEwen |
| 4,979,953 A | 12/1990 | Spence |
| B1 4,469,099 A | 11/1992 | McEwen |
| 5,454,831 A | 10/1995 | McEwen |
| 5,584,853 A | 12/1996 | McEwen |
| 5,607,447 A | 3/1997 | McEwen et al. |
| 5,649,954 A | 7/1997 | McEwen |
| 5,690,672 A | 11/1997 | Cohen |
| 5,741,295 A | 4/1998 | McEwen |
| 5,746,213 A | 5/1998 | Marks |
| 5,823,012 A * | 10/1998 | Hacskaylo ................... 66/171 |

OTHER PUBLICATIONS

AORN, Recommended Practices for Use of the Pneumatic Tourniquet, from *AORN Standards, Practices and Guidelines*, 1999, pp. 283–287.

Henderson et al., A North American Survey of Intravenous Regional Anesthesia, from Anesthesia & Analgesia 1997; 85:858–863.

Operator and Service Manual—A.T.S. 2000 Tourniquet System, Zimmer Inc. (Warsaw, IN), pp. 1–6.

Richards Disposable Tourniquet Cuffs Important General Use Guidelines, from Smith & Nephew Richards Inc. (Memphis TN), 3 pages.

* cited by examiner

Primary Examiner—Henry J. Recla
(74) Attorney, Agent, or Firm—Ipsolon LLP (57) ABSTRACT

Limb protection sleeve matches a specific tourniquet cuff for application to limbs having circumferences between minimum and a maximum circumference so that the sleeve, after application to a limb of minimum circumference, stretches elastically and so that the sleeve, after application to a limb of maximum circumference, applies a pressure to the limb that is less than a predetermined maximum pressure.

7 Claims, 6 Drawing Sheets

LIMB PROTECTION SLEEVE FOR MATCHING TOURNIQUET CUFF

FIELD OF THE INVENTION

This invention generally pertains to surgical tourniquets. The invention particularly pertains to surgical tourniquet cuffs for encircling and applying pressure to patients' limbs in order to stop blood flow into the limbs and to limb protection sleeves matched to the cuffs for interposing between the limbs and the cuffs to help protect the limbs from cuff-related injuries during surgical procedures.

BACKGROUND

Surgical tourniquet cuffs typically are applied to a patient's limb at a desired location and are then pressurized in order to stop the flow of arterial blood past the cuff, thereby establishing a bloodless field in the portion of the limb distal to the cuff. The structure and function of some typical tourniquet cuffs of the prior art are described by Robinette-Lehmann in U.S. Pat. No. 4,635,635, by Spence in U.S. Pat. No. 4,979,953 and by McEwen in U.S. Pat. Nos. 5,454,831 and 5,649,954. The pressure applied by such prior-art tourniquet cuffs is typically controlled by electronic tourniquet apparatus such as that described by McEwen in U.S. Pat. No. 4,469,099 by McEwen and Jameson in U.S. Pat. No. 5,607,447.

The bloodless surgical field created by a pressurized tourniquet cuff facilitates many types of surgical procedures performed on upper limbs and lower limbs, helps improve the quality and consistency of the surgical procedures, reduces the need for blood transfusions, and shortens surgical times. In certain kinds of surgical procedures, only the portion of the limb distal to the tourniquet cuff is anesthetized using a procedure called Bier block anesthesia or Intravenous Regional Anesthesia (IVRA); in such procedures, the tourniquet cuff performs a dual function of keeping the anesthetic agent in the limb and keeping arterial blood out of the limb. Clinical practice involving the use of tourniquets in IVRA was recently summarized in a paper by Henderson et al. entitled "A North American Survey of Intravenous Regional Anesthesia" published in Anesthesia and Analgesia (1997; 85:858–863).

In an effort to reduce the probability of certain injuries to the soft tissues of the limb beneath a pressurized tourniquet cuff, some operators may elect to apply a soft bandage to the limb beneath the cuff. For example, in "Recommended Practices for Use of the Pneumatic Tourniquet", published by the Association of Operating Room Nurses (AORN) in the United States and effective as of Jan. 1, 1999, it is noted that "The cuff should be applied to the extremity so that underlying skin and soft tissue are not unduly traumatized. Manufacturers' instructions may suggest that a soft, wrinkle-free padding (eg, cotton cast padding, stockinette) be wrapped smoothly around the limb as high on the extremity as possible, being careful not to pinch the skin folds where the tourniquet is applied. Once inflated the cuff should not be readjusted. Users must note that some tourniquet technology does not require padding."

In the prior art, soft bandages that have been used in conjunction with tourniquet cuffs have included sheet padding combined with a fluid-impervious layer and an adhesive tab as described by Hubbard et al. in U.S. Pat. No. 4,406,281, as well as cast padding of the type wrapped around a broken limb before a cast is applied. Proper application of these soft bandages in conjunction with tourniquet cuff usage is very technique-dependent, requiring a trained and experienced applicator. Further, some types of padding may release loose fibers when applied, and these fibers may enter the surgical field and may clog the hook-and-loop fasteners that are typically used to secure tourniquet cuffs in position around the limb, thereby reducing the effective strength of these fasteners and creating a potential hazard. Also, the padding itself may take on a non-uniform shape around the limb, especially when an overlying tourniquet cuff is inflated. Finally, if too much soft bandage is used or if it is applied improperly, then hazards may arise because the level of pressure required in the tourniquet cuff to stop blood flow past the cuff may increase substantially, and the position of the cuff on the limb may become unstable after inflation, increasing the likelihood that the cuff position may change significantly relative to the limb during use.

An alternative to the use of soft bandages and cast padding in the prior art has been to use tubular stockinette between the patient's limb and the tourniquet cuff. Typically, tubular stockinette is made and supplied in a wide range of predetermined 'lay-flat' widths, knits and materials. Tubular stockinette consists of a knitted textile having a substantially cylindrical shape in which some of the knitted threads either are elastic or are knitted in a manner that permits elastic stretching of the tubular shape. In appearance, tubular stockinette resembles the ankle portion of a sock or the leg portion of a nylon stocking. Elastic threads are included in some types of tubular stockinette to give them stretch and elastic characteristics that are a function of the type and number of elastic and non-elastic threads used in the knit and the knit pattern itself. In other types of stockinette that are knitted from non-elastic threads, the stretch and elastic characteristics of the stockinette are primarily determined by the type of knit. Two general advantages of using tubular stockinette under a tourniquet cuff, in comparison to overlapping soft bandages, are: tubular stockinette does not shed loose fibers which can enter the surgical field and clog cuff fasteners; and tubular stockinette does not produce as non-uniform a shape around the limb as soft bandages may do.

There are a number of limitations associated with such prior-art tubular stockinette. The most important limitation is that the pressure applied to the encircled limb by the tubular stockinette may be too high or too low. If the tubular stockinette is stretched excessively to fit around the limb at the desired cuff location, too high a pressure may result: in such situations, the pressure applied to the limb by the elastically stretched tubular stockinette may be sufficiently high to stop the flow of venous blood out of the limb and impair the flow of arterial blood into the limb.

Because of the concern about residual pressures that might be applied by tubular stockinette, one manufacturer of prior-art tourniquet cuffs and instruments (Zimmer, Warsaw Ind.) cautions on page 6 of the Operator and Service Manual for its A.T.S. 2000 Automatic Tourniquet System that "As an under padding, a section of stockinette may be used. The deflated cuff and any underlying bandages should be completely removed as soon as tourniquet pressure is released. Even the slightest impedance of venous return may lead to congestion and pooling of blood in the operative field." Similar cautions and warnings about hazards related to the residual application of non-pneumatic pressure by underlying padding such as stockinette, as well as tourniquet cuffs, are given by other suppliers of tourniquet-related products and in the surgical literature.

Alternatively, if the tubular stockinette is not stretched at all, or if it is not stretched sufficiently at a desired cuff location, then the tubular stockinette may apply no pressure to the underlying limb and inflation of an overlying tourniquet cuff may then produce folding and wrinkling of the tubular stockinette material. This can cause soft tissue injuries resulting from pinching, folding and shearing of skin beneath the tubular stockinette, as well as causing other hazards arising from local anomalies in the pressure applied to the limb beneath the tubular stockinette by the inflated cuff and from the increased inflation pressure that may be required in the cuff to stop blood flow.

One commercial product is known in the prior art that combines tubular stockinette and a single-use tourniquet cuff in a single sterile package (Smith and Nephew Richards Inc., Memphis, Tenn.). The tubular stockinette consists of a substantially cylindrical length of elastically stretchable knitted fabric that has been folded back on itself twice, so that by pulling the tubular stockinette up a limb to a desired cuff location, the tourniquet cuff can be applied over four layers of stretched stockinette material. The tourniquet cuff can be applied to limbs having a wide range of circumferences. However, over much of that range, the stockinette is too large. The circumference of the unstretched stockinette is greater than much of the range of circumferences of limbs on which the cuff may be applied. This is hazardous because, as noted above, if the tubular stockinette is loose and not elastically stretched to some extent at the desired cuff location on a limb prior to application of the tourniquet cuff, then the application and inflation of the cuff over the stockinette will produce folding and wrinkling of the underlying stockinette material, increasing the likelihood of soft tissue injuries due to pinching, folding and shearing of skin beneath the stockinette, as well as creating other surgical and IVRA-related hazards arising from local anomalies in the pressure applied to the limb and from the higher pressures that must be applied onto such stockinette by the encircling tourniquet cuff to stop blood flow in the underlying limb.

The pressure applied by a tubular stockinette to a limb of a given shape, circumference and tissue composition can be measured using a biomedical pressure transducer such as the one described by McEwen in U.S. Pat. No. 4,869,265. Using such a transducer, it is has been found in tests conducted by the inventor that pressures from 0 mmHg to more than 60 mmHg can applied to limbs of varying circumferences and physical properties by prior-art tubular stockinettes of varying sizes, materials, knits and designs. For comparison, it has been found that an applied pressure as low as 30 mmHg can partially or completely obstruct venous blood flow, and that applied pressures lower than 60 mmHg can impede and partially block arterial blood flow.

In the prior art, there is no known limb protection sleeve that matches a specific tourniquet cuff for application to limbs having circumferences between a minimum and a maximum circumference so that the sleeve, after application to a limb of minimum circumference, stretches elastically and so that the sleeve, after application to a limb of maximum circumference, applies a pressure to the limb that is less than a predetermined maximum pressure.

DESCRIPTION OF THE PREFERRED EMBODIMENT

The embodiment illustrated is not intended to be exhaustive or limit the invention to the precise form disclosed. It is chosen and described in order to explain the principles of the invention and its application and practical use, and thereby enable others skilled in the art to utilize the invention.

Figure 1:
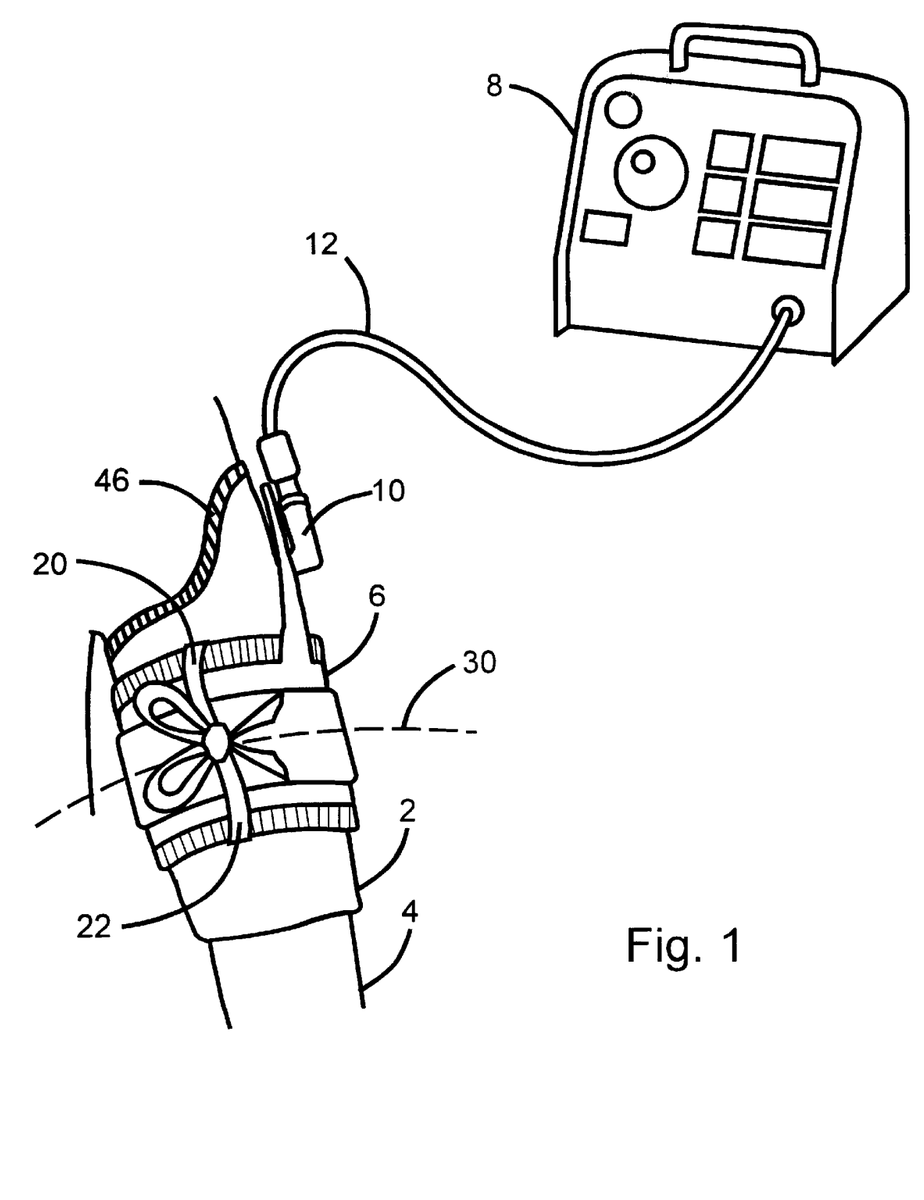
FIG. 1 is a pictorial representation of the preferred embodiment applied to a limb of a surgical patient.

FIG. 1 depicts the preferred embodiment applied to a limb of a surgical patient. Limb protection sleeve 2 has been applied by a user to limb 4 along a portion of its length. Inflatable tourniquet cuff 6 is applied on top of a proximal portion of limb protection sleeve 2 to encircle the portion of sleeve 2 and limb 4 at a location desired by a user. Cuff 6 is pneumatically connected to tourniquet instrument 8 through pneumatic port 10 and pneumatic tubing 12. Prior to the commencement of surgery, the portion of sleeve 2 distal to cuff 6 is folded back on top of cuff 6 by the user, as depicted in FIG. 6c. Tourniquet instrument 8 can then supply gas to tourniquet cuff 6 at a pressure sufficient to stop blood flow in limb 4 past cuff 6 and sleeve 2 for a time period sufficient for the performance of a surgical procedure.

Figure 2:
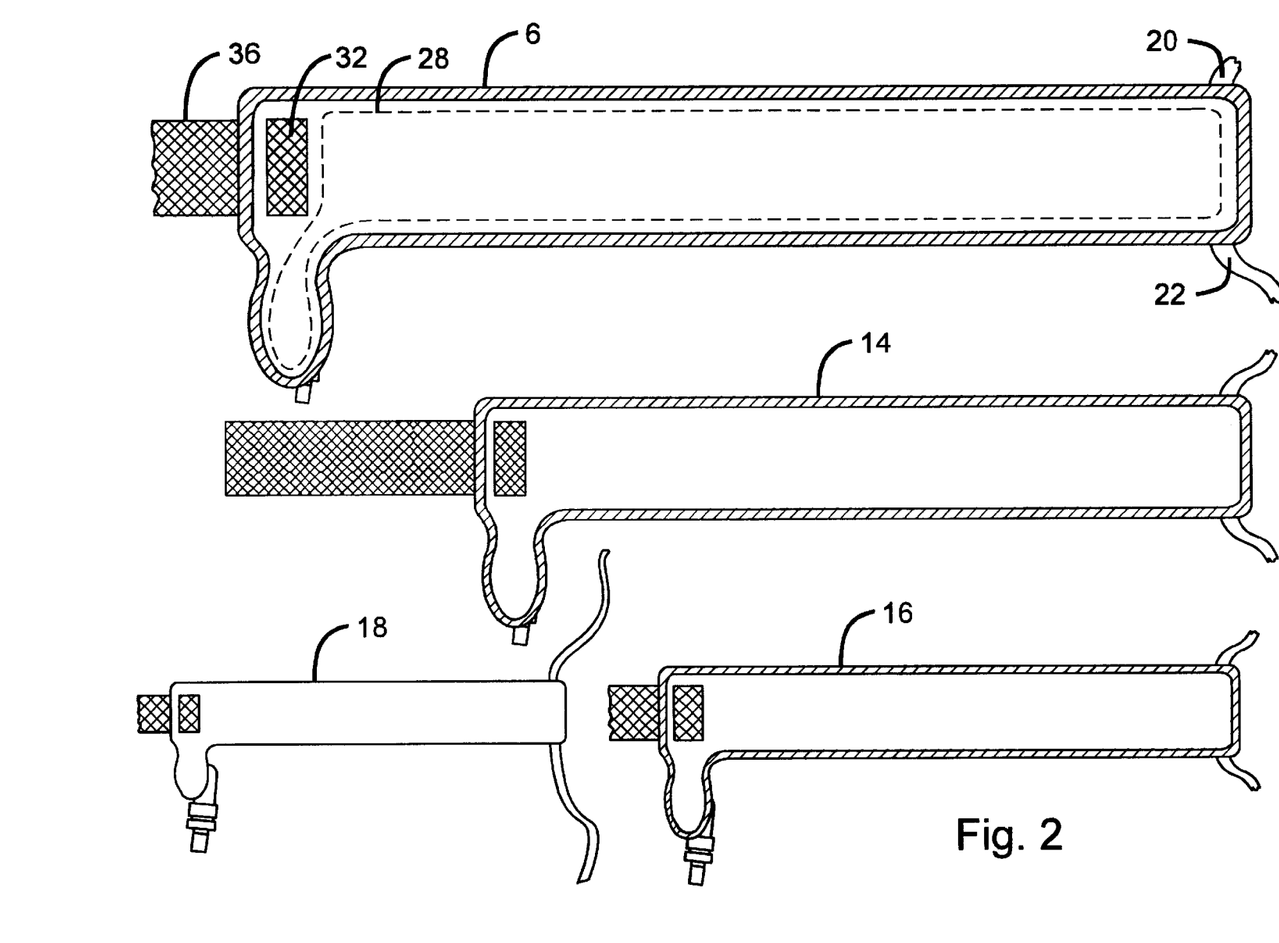
FIG. 2 depicts the inner surfaces of four tourniquet cuffs of similar design and different sizes.

FIG. 2 depicts the inner surfaces of tourniquet cuff 6, cuff 14, cuff 16 and cuff 18, which are pediatric tourniquet cuffs of different sizes that are distributed by Delfi Medical Innovations Inc. (Vancouver, Canada). Each of cuffs 6, 14, 16 and 18 is constructed of materials and in a manner generally similar to tourniquet cuffs of the prior art such as those described by McEwen in U.S. Pat. Nos. 5,454,831 and 5,649,954.

Cuffs 6, 14, 16 and 18 shown in FIG. 2 have overall cuff width and cuff length dimensions as given in the table below. Also, for each of cuffs 6, 14, 16 and 18, the table shows the maximum limb circumference and the minimum limb circumference recommended by the distributor in the product literature and instructions provided for users. To assist users in easily identifying and differentiating among cuffs, the tie straps of different cuffs have different colors: cuffs 6, 14 16 and 18 have green, red, blue and black tie straps, respectively, as summarized in the table.

| Cuff no. from FIG. 2 (and color of tie straps) | Overall Cuff Length (inches) | Overall Cuff Width (inches) | Recommended Minimum Limb Circumference (inches) | Recommended Maximum Limb Circumference (inches) |
| --- | --- | --- | --- | --- |
| 6 (green) | 17.7 | 3.50 | 8.3 | 15.3 |
| 14 (red) | 14.9 | 3.00 | 6.9 | 12.5 |
| 16 (blue) | 10.6 | 2.25 | 4.9 | 8.3 |
| 18 (black) | 7.5 | 1.50 | 3.5 | 5.6 |

Figure 3:
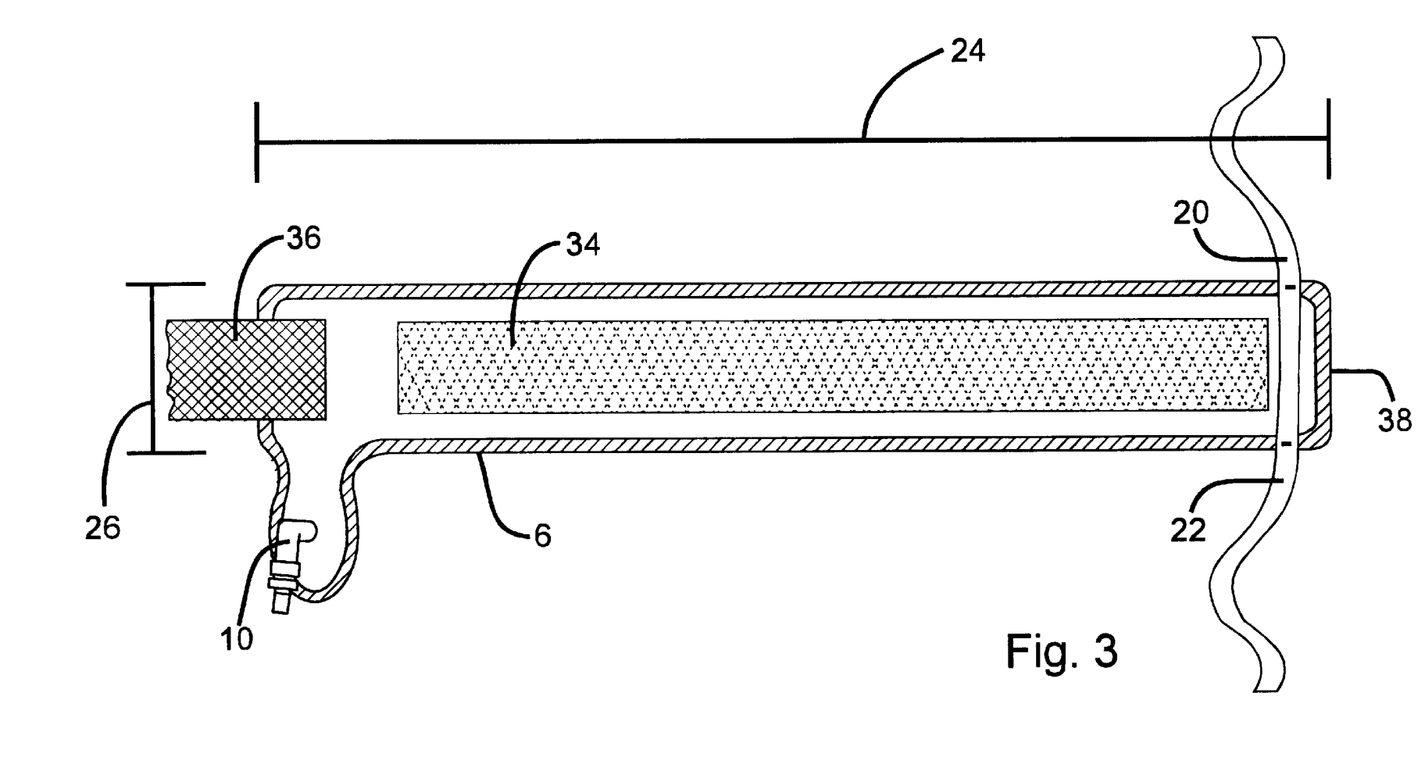
FIG. 3 shows the outer surface of one of the tourniquet cuffs depicted in FIG. 2.

FIG. 3 shows the outer surface of cuff 6 that faces away from limb 4 when cuff 6 encircles limb 4. The length 24 of cuff 6 is 17.7 inches and the width 26 of cuff 6 is 3.50 inches. Cuff 6 contains an inflatable chamber 28, the boundary of which can be seen in FIG. 2. Cuff 6 is designed to allow a user to encircle a patient's limb 4 at a desired location 30 so that a portion of inflatable chamber 28 of cuff 6 overlaps upon itself, and so that the user can secure encircled cuff 6 around limb 4 by fully engaging primary cuff fastener 32 to fastening strip 34 and by fully engaging secondary cuff fastener 36 to fastening strip 34. Complementary hook and loop materials, such as those known in the prior art as Velcro™, are permanently attached in positions shown in FIGS. 2 and 3 to form primary cuff fastener 32, fastening strip 34 and secondary cuff fastener 36. Primary cuff fastener 32 and secondary cuff fastener 36 are formed of hook material, and fastening strip 34 is formed of loop material. The user may also tie together tie straps 20 and 22 as depicted in FIG. 1 to secure cuff end 38. When secured around limb 4 and inflated with gas from tourniquet instrument 8 at a sufficient pressure, cuff 6 can apply pressure around encircled limb 4 to stop the flow of arterial blood past cuff 6 into limb 4.

Cuff 6 is further designed to encircle limb 4 if limb 4 has a limb circumference greater than 8.3 inches and less than 15.3 inches at location 30, as specified in product literature and instructions provided by the distributor for the user. As illustrated in FIGS. 1, 2 and 3, when cuff 6 is applied to limb 4 at location 30 having a circumference between the maximum and minimum circumferences recommended to the user, then the following four conditions occur: (1) a portion of inflatable chamber 28 overlaps upon itself around limb 4, thereby producing a uniform application of pressure around limb 4 when chamber 28 is inflated, (2) primary cuff fastener 32 can be fully engaged with fastening strip 34 by the user to secure cuff 6 around limb 4, (3) secondary cuff fastener 36 can also be fully engaged with fastening strip 34 by the user to secure cuff 6 around limb 4 independently of primary cuff fastener 32, and (4) tie straps 20 and 22 can be tied together by the user to secure cuff end 38.

If the circumference of limb 4 at location 30 is greater than the maximum circumference of 15.3 inches recommended to the user, then cuff 6 may not safely stop blood flow because of the occurrence of one or more of the following three conditions: (1) primary cuff fastener 32 may not fully engage with fastening strip 34; (2) inflatable chamber 28 may not overlap upon itself around limb 4, thereby producing a non-uniform application of pressure around the limb when inflated; and (3) tie straps 20 and 22 may be obstructed by pneumatic port 10 of cuff 6, thereby preventing straps 20 and 22 from being tied together to secure cuff end 38.

Alternatively, if the circumference of limb 4 at location 30 is less that the minimum circumference of 8.3 inches, then the efficacy and safety of cuff 6 may be impaired by the occurrence of one or more of the following four conditions: (1) the width of cuff 6 may be excessive relative to the length of limb 4, resulting in hazardous application of pressure by cuff 6 to nerves and soft tissues near the knee or elbow joints of lower or upper limbs respectively; (2) the width of cuff 6 may be excessive relative to the length of limb 4, increasing the obstruction of potential surgical sites distal to cuff 6; (3) secondary cuff fastener 36 may not fully engage with fastening strip 34; (4) tie straps 20 and 22 may be obstructed by pneumatic port 10 of cuff 6, thereby preventing straps 20 and 22 from being tied together to secure cuff end 38.

Limb protection sleeve 2 of the preferred embodiment is designed for use with tourniquet cuff 6 by designing sleeve 2 to have the following physical properties: (a) it has a tubular and elastically stretchable shape, with an unstretched circumference of less than the minimum limb circumference recommended for cuff 6 so that it is elastically stretched when applied to a limb having the minimum recommended circumference; (b) it can be elastically stretched in a radial direction to a circumference at least equal to the maximum limb circumference recommended for cuff 6; (c) when elastically stretched and applied to a limb having the maximum recommended circumference, the maximum pressure applied to the underlying limb by sleeve 2 is less than the pressure that would normally result from the snug application of cuff 6 alone to the limb; and (4) when applied to a limb having the maximum recommended circumference, the length of sleeve 2 is greater than the width of cuff 6, so that a portion of sleeve 2 can be folded over cuff 6 prior to the commencement of surgery, as shown in FIG. 6c.

Figure 4A:
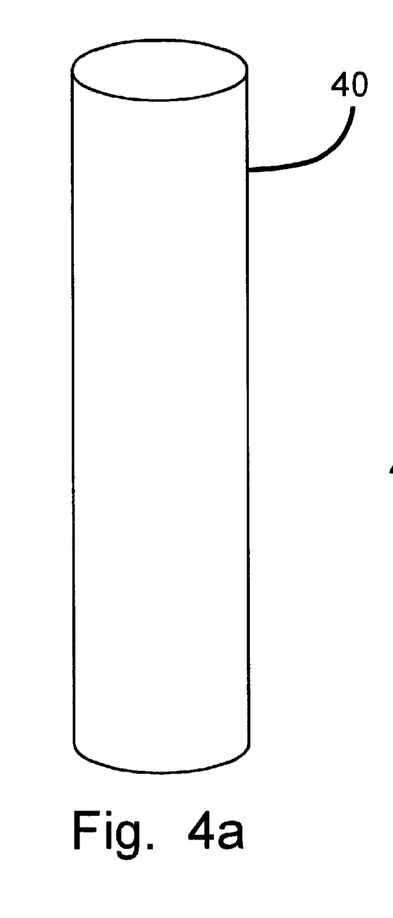
FIGS. 4a, 4b and 4c show steps in the manufacture of a limb protection sleeve matching the tourniquet cuff shown in FIG. 3.
Figure 4B:
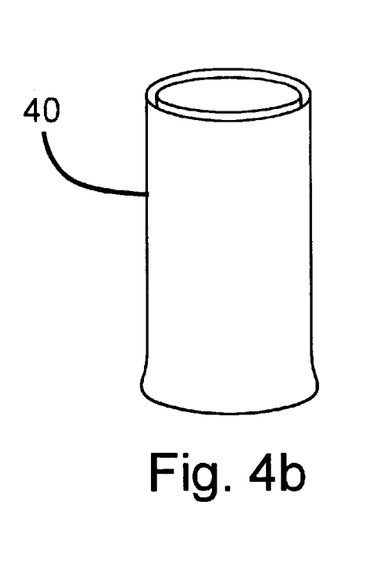
Figure 4C:
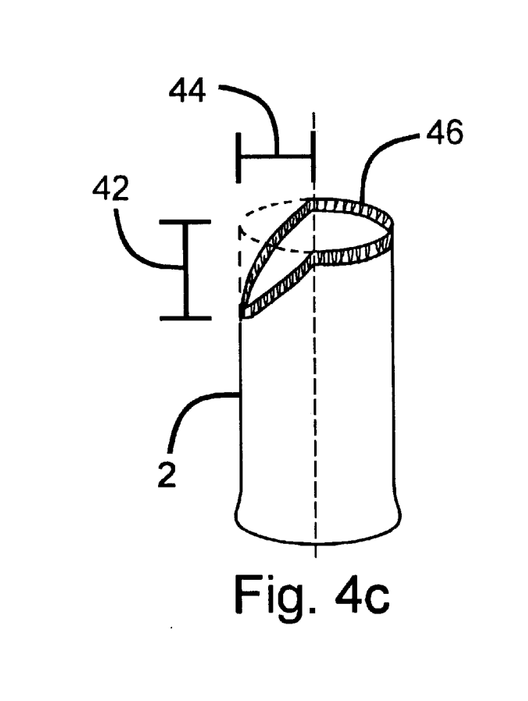

FIGS. 4a, 4b and 4c show how limb protection sleeve 2 is designed and made to match cuff 6 by having the physical properties described above. First, tubular stockinette 40 shown in FIG. 4a is produced by knitting type 18/1 ring spun cotton yarn fiber of natural color using 160 needles and 25 courses per inch. This results in tubular stockinette 40 having a circumference of 7.0 inches (twice a "layflat" width of about 3.5 inches) when not stretched in a radial direction, and having a maximum circumference of 26 inches (twice a "cross stretch" width of 13 inches) when stretched radially to the maximum. Stockinette 40 is cut to a length of 22.0 inches and folded back onto itself as shown in FIG. 4b, producing a tube having two layers and a length of 11.0 inches when unstretched. As depicted in FIG. 4c, the unfolded end is bias cut. This is done with the stockinette laid flat, to remove a piece having length 42 equal to 2.5 inches and width 44 equal to half of the layflat width of the stockinette, as shown in FIG. 4c. The unfolded end that includes the bias cut is then serge-sewn with green thread to produce limb protection sleeve 2 having a green edge 46. As indicated in FIG. 1, the bias cut of sleeve 2 allows sleeve 2 to be positioned as proximally as possible on limb 4 while still protecting a portion of limb 4 from port 10 and tubing 12. Sewn edge 2 increases the stability of dual-layer sleeve 2 under matching cuff 6 when cuff 6 is inflated and pressurized to stop blood flow, and the knit shape of sleeve 2 is compressible in response to the application of the pressure by matching cuff 6.

To confirm that the design of sleeve 2 of the preferred embodiment, as described above, produces the necessary physical properties, sleeve 2 is applied to cover a simulated limb having a circumference equal to 15.3 inches, the maximum circumference recommended for matching cuff 6. A biomedical pressure transducer similar to that described by McEwen in U.S. Pat. No. 4,869,265 is inserted between sleeve 2 and the simulated limb to measure the applied pressure. The maximum pressure applied by sleeve 2, as measured by the transducer in these design validation tests, is less than 15 mmHg, a pressure known from previous testing done by the applicant to be substantially less than the maximum non-pneumatic pressure of approximately 25 mmHg that typically can be produced by a tourniquet cuff when snugly applied to a limb by a user. Also, sleeve 2 is applied to cover a simulated limb having a circumference equal to 8.3 inches, the minimum circumference recommended for matching cuff 6, to confirm that sleeve 2 is elastically stretched after application, thus minimizing any residual wrinkling and irregularities, and to confirm using the same pressure transducer that the pressure applied to the simulated limb of minimum circumference by the elastically stretched sleeve is substantially less than 25 mmHg, the maximum non-pneumatic pressure that typically can be produced by a tourniquet cuff when snugly applied to a limb by a user.

The color of green edge 46 allows a user to visually match sleeve 2 to tourniquet cuff 6 having green tie straps 20 and 22. Although a common color is used in the preferred embodiment to associate sleeve 2 and cuff 6, it will be appreciated by those skilled in the art that alternate means might be used, such as marking numbers, letters or symbols directly on sleeve 2 and cuff 6 or on packages containing each. If cuff 6 and sleeve 2 are both designed as disposable medical devices, intended for use in only one surgical procedure and disposal after the procedure without re-use on another patient, then an alternate way of matching sleeve 2 and cuff 6 for the user is to package them together at time of manufacture, for example by putting them in the same bag or box.

Figure 5:
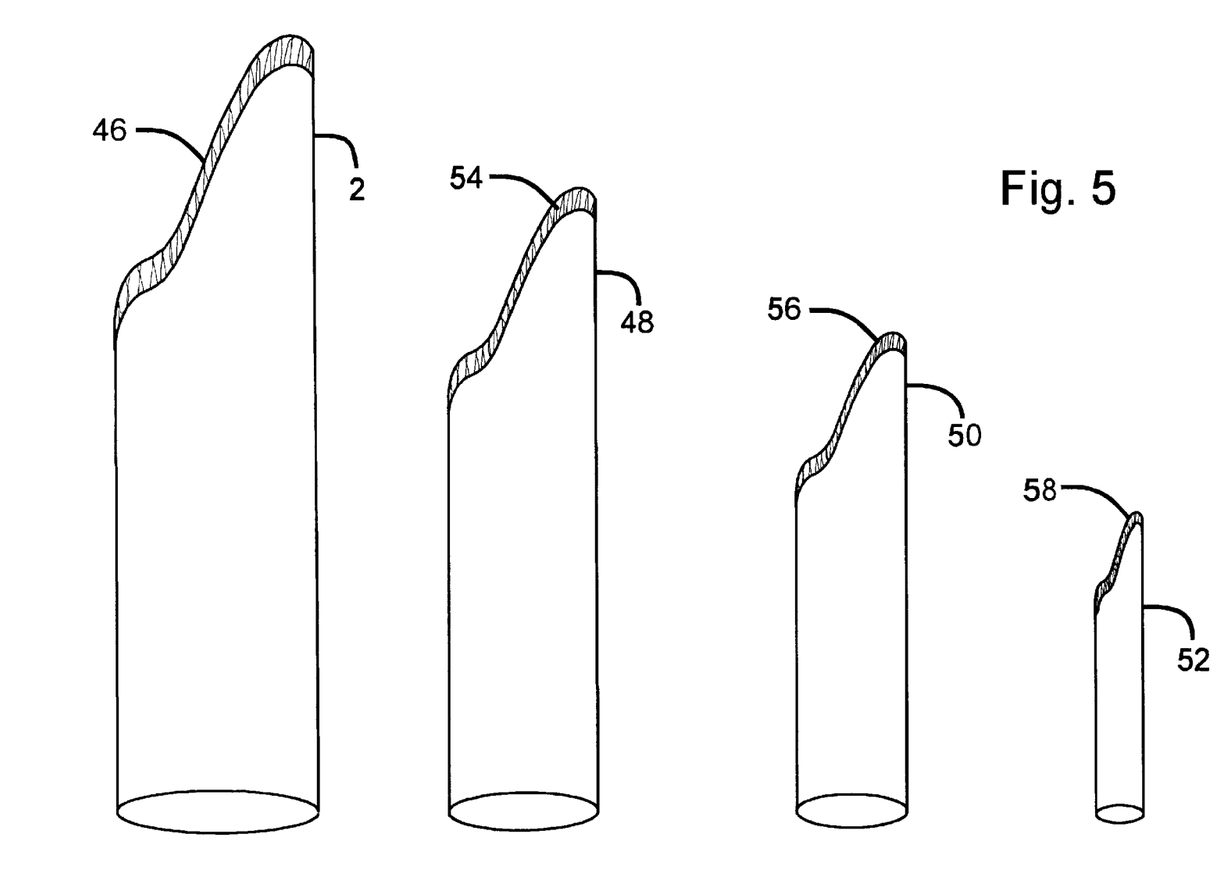
FIG. 5 shows four limb protection sleeves that match the four tourniquet cuffs depicted in FIG. 2.

FIG. 5 shows four sizes of limb protection sleeves 2, 48, 50 and 52 that are matched to tourniquet cuffs 6, 14, 16 and 18 respectively. Sleeves 48, 50 and 52 are designed, manufactured and validated as described above for sleeve 2, except that each has a different length, unstretched circumference, circumference at maximum stretch, and edge color. Sleeve 48 matches cuff 14 and is produced by: (a) knitting the same type of cotton fiber using 124 needles and 23 courses per inch, resulting in tubular stockinette having a circumference of 5.0 inches when not stretched in a radial direction, and having a maximum circumference of 18.0 inches when stretched radially to the maximum; (b) cutting the stockinette and folding it back onto itself to create a tube having two layers and a length of 9.5 inches, and (c) bias cutting an unfolded edge and serging the cut edge with red thread to produce red edge 54 matching the red tie straps of cuff 14. Sleeve 50 matches cuff 16 and is produced by: (a) knitting the same type of fiber using 70 needles and 22 courses per inch, resulting in tubular stockinette having a circumference of 3.0 inches when not stretched in a radial direction, and having a maximum circumference of 13.0 inches when stretched radially to the maximum; (b) cutting the stockinette and folding it back onto itself to create a tube having two layers and a length of 8.0 inches, and (c) bias cutting the unfolded edge and serging the cut edge with blue thread to produce blue edge 56 matching the blue tie straps of cuff 6. Sleeve 52 matches cuff 18 and is produced by (a) knitting the cotton yarn fiber using 40 needles and 21 courses per inch, resulting in tubular stockinette having a circumference of 1.5 inches when not stretched in a radial direction, and having a maximum circumference of 7.0 inches when stretched radially to the maximum; (b) cutting the tubular stockinette and folding it back onto itself to create a tube having two layers and a length of 7.0 inches, and (c) bias cutting the unfolded edge and serging the cut edge with black thread to produce black edge 58 matching the black tie straps of cuff 18.

For each of limb protection sleeves 2, 48, 50 and 52 shown in FIG. 5, the table below summarizes the respective sleeve length, sleeve edge color, unstretched sleeve circumference, maximally stretched sleeve circumference, matching cuff, and the recommended minimum and maximum limb circumferences for sleeve and matching cuff.

| Limb protection Sleeve (in FIG. 5): | 2 | 48 | 50 | 52 |
|---|---|---|---|---|
| Sleeve length (inches) | 11.0 | 9.5 | 8.0 | 7.0 |
| Sleeve edge color | Green | Red | Blue | Black |
| Sleeve circumference: | | | | |
| Unstretched (in): | 7.0 | 5.0 | 3.0 | 1.5 |
| Max. stretch (in): | 26.0 | 18.0 | 13.0 | 7.0 |
| Matching cuff (FIG. 2) | 2 | 14 | 16 | 18 |
| Color of tie straps | Green | Red | Blue | Black |
| Recommended limb Circumferences for | | | | |

| -continued | | | | |
|---|---|---|---|---|
| Limb protection Sleeve (in FIG. 5): | 2 | 48 | 50 | 52 |
| cuff and sleeve: | | | | |
| Minimum (inches): | 8.3 | 6.9 | 4.9 | 3.5 |
| Maximum (inches): | 15.3 | 12.5 | 8.3 | 5.6 |

Figure 6A:
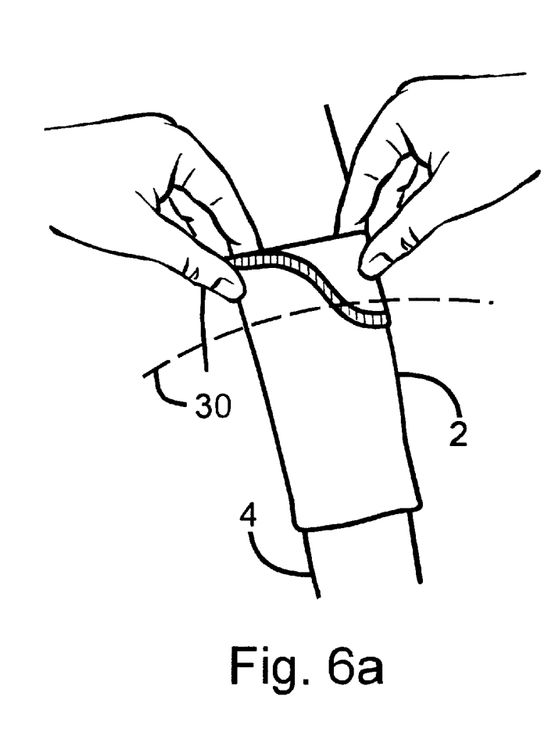
FIGS. 6a, 6b and 6c illustrate steps in a typical selection and application of a tourniquet cuff and matching limb protection sleeve to a patient's limb by a user.
Figure 6B:
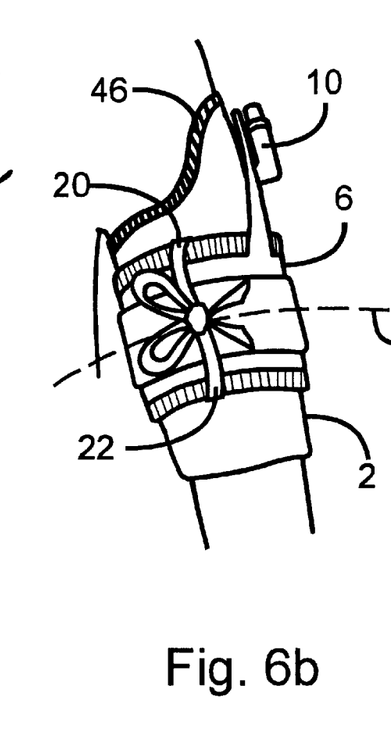
Figure 6C:
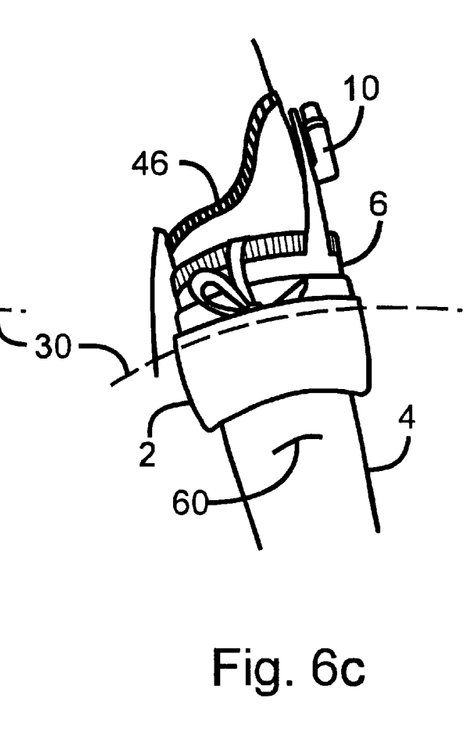

FIGS. 6a, 6b and 6c illustrates steps in a typical selection and application of a tourniquet cuff and matching limb protection sleeve to limb 4 by a user. Prior to these steps, the user first observes the location 30 on limb 4 where it is desired to apply a tourniquet cuff and sleeve. The user then selects from the available sizes of cuffs the widest cuff that can: (a) fully encircle limb 4 at location 30 with a portion of the cuff overlapping upon itself, (b) allow the primary and secondary cuff fasteners to be fully engaged by the user, and (c) leave a safe distance between the distal edge of the selected cuff and joint 60 of limb 4 that is immediately distal location 30. The operating surgeon is responsible for determining this safe distance for each patient, to prevent injury to exposed nerves, vessels and soft tissue near joint 60. After the cuff is selected, the matching limb protection sleeve is selected; in the preferred embodiment, this is done by matching the color of the tie straps of the cuff to the color of the sewn edge of the sleeve. FIGS. 6a, 6b and 6c indicate that cuff 6 and matching sleeve 2 have been selected for application at desired location 30 on limb 4. The user slides selected sleeve 2 onto limb 4 over location 30 as illustrated in FIG. 6a, and after application assures that sleeve 2 is free of wrinkles and that the colored edge 46 of sleeve 2 is positioned as shown in FIG. 6a to help protect limb 4 from port 10 and tubing 12. As shown in FIG. 6b, after application of sleeve 2, selected cuff 6 is wrapped snugly around the proximal portion of sleeve 2 and limb 4 at the desired location, while assuring that port 10 is positioned over sleeve 2 as shown. After snug application of cuff 6 by the user, the portion of sleeve 2 distal to cuff 6 is folded back over cuff 6 as shown in FIG. 6c. The operating surgeon then observes cuff 6 and sleeve 2 as applied, to assure that there is still a safe distance between joint 60 and applied cuff 6 and sleeve 2. The user can then connect tubing 12 to port 10 and inflate cuff 6 using tourniquet instrument 8 to stop blood flow for the performance of a surgical procedure. Immediately upon deflation of cuff 6, both cuff 6 and sleeve 2 are immediately removed from limb 4 to remove any residual restriction of blood flow.

It is to be understood that the invention is not to be limited to the details herein given but may be modified within the scope of the appended claims.

I claim:

1. Apparatus for protecting a patient's limb from tourniquet-related injury, comprising:
a tourniquet cuff having a length sufficient for encircling a limb having a limb circumference within a range of not less than a predetermined minimum and not more than a predetermined maximum, and wherein the cuff has a first indicium thereon that is indicative of that range, and wherein the cuff forms a generally cylindrical shape when encircling the limb and includes a protruding port portion;
a stretchable limb protection sleeve having a tubular shape and an unstretched circumference that is less than the predetermined minimum, the sleeve including a proximal edge and a distal edge, the proximal edge being shaped to have a protrusion such that the width of the sleeve varies between the proximal edge and the distal edge, and wherein the protrusion of the sleeve is underlies the port portion when the sleeve is applied to the limb beneath the cuff; and matching means carried on the sleeve and perceptible to a user for matching the sleeve to the first indicium of the cuff.

2. The apparatus of claim 1 wherein the matching means includes a second indicium on the sleeve that corresponds to the first indicium on the cuff.

3. The apparatus of claim 2 wherein the sleeve is comprised of two layers, with one layer folded over another layer at a fold edge and so that the edges of the layers away from the fold edge are sewn together at a sewn edge of the sleeve.

4. The apparatus of claim 3 wherein the second indicium is incorporated into the sewn edge of the sleeve.

5. The apparatus of claim 1 wherein the cuff has a predetermined width and forms a generally cylindrical shape when encircling the limb, and whereby the sleeve is sized to be substantially wider than the cuff thereby to enable part of the sleeve to underlie the cuff around the limb while another part of the sleeve is folded over the cuff when the cuff encircles the limb.

6. The apparatus of claim 1 further comprising an instrument attached to the cuff for pressurizing the cuff.

7. The apparatus of claim 2 wherein the first indicium and the second indicium are the same color.

\* \* \* \* \*